US007241623B2

(12) United States Patent
Balazs et al.

(10) Patent No.: US 7,241,623 B2
(45) Date of Patent: Jul. 10, 2007

(54) LITHIUM DETECTION IN LIQUID BIOLOGICAL SAMPLES AND REAGENTS THEREFOR

(75) Inventors: Nicholas Dennis Henry Balazs, Burnley (AU); John William Secombe, Elwood (AU)

(73) Assignee: Seba Diagnostics Pty. Ltd. (AU)

( * ) Notice: Subject to any disclaimer, the term of this patent is extended or adjusted under 35 U.S.C. 154(b) by 115 days.

(21) Appl. No.: 10/296,592

(22) PCT Filed: May 25, 2001

(86) PCT No.: PCT/AU01/00603

§ 371 (c)(1),
(2), (4) Date: Jun. 4, 2003

(87) PCT Pub. No.: WO01/92881

PCT Pub. Date: Dec. 6, 2001

(65) Prior Publication Data

US 2003/0186450 A1     Oct. 2, 2003

(30) Foreign Application Priority Data

May 26, 2000     (AU) .................... PCT/AU01/00603

(51) Int. Cl.
*G01N 33/20* (2006.01)
(52) U.S. Cl. .............................. 436/79; 422/61; 436/73; 436/164; 436/166; 436/172
(58) Field of Classification Search ............ 422/61; 436/73, 79, 164, 166, 172
See application file for complete search history.

(56) References Cited

U.S. PATENT DOCUMENTS

| | | | | |
|---|---|---|---|---|
| 4,599,316 A | * | 7/1986 | Hahn et al. ............... | 436/105 |
| 4,859,606 A | * | 8/1989 | Cram et al. ............... | 436/79 |
| 5,055,388 A | * | 10/1991 | Vogt et al. ................ | 435/4 |
| 5,110,742 A | * | 5/1992 | Shu et al. ................. | 205/781.5 |
| 5,187,103 A | | 2/1993 | Czech et al. | |
| 5,300,439 A | | 4/1994 | Charlton | |
| 5,340,714 A | * | 8/1994 | Katsilometes ............. | 435/6 |
| 5,344,782 A | | 9/1994 | Lin et al. | |

FOREIGN PATENT DOCUMENTS

| | | |
|---|---|---|
| EP | 0 579 331 A1 | 1/1994 |
| WO | WO 96/02839 A1 | 2/1996 |

OTHER PUBLICATIONS

Semichaevskii, V. D. Chemical Abstracts 1975, 82, abstract 167620g.*
Hinoue, T. et al, Chemistry Letters 1997, 763-764.*
Gandini, S. C. M. et al, Langmuir 1999, 15, 6233-6243.*
Li, Xi-you et al, Macromolecules 2000, 33, 2119-2123.*
Semichaevskii, V. D., Fiziologiya i Biokhimiya Kul'turnykh Rastenii 1975, 7, 18-24.*
Jacox, R. F., Journal of Clinical Investigation 1953, 32, 661-673.*
Jirgensons, B. et al, Makromolekulare Chemie 1963, 60, 25-44.*
Canioni, P. et al, Lipids 1980, 15, 6-9.*
Gonzalez-Vergara, E. et al, Biochemistry 1985, 24, 6561-6567.*
Kano, K. et al, Bulletin of the Chemical Society of Japan 1987, 60, 1281-1287.*
Venkatesh, B. et al, Biochemical and Biophysical Research Communications 1996, 223, 390-396.*
Richards, R.A., et al., "Observation of a Stable Water-Soluble Lithium Porphyrin," *Inorg. Chem.* 35:1940-1944, American Chemical Society (1996).
Sun, H., and Tabata, M., "Separation and transport of lithium of $10^{-5}$ M in the presence of sodium chloride higher than 0.1 M by 2,3,7,8,12,13,17,18-octabromo-5,10,15,20-tetrakis (4-sulfonatophenyl)porphyrin," *Talanta* 49:603-610, Elsevier Science B.V. (Jul. 1999).
Tabata, M., et al., "Metalation of Water-Soluble Octabromoporphyrin with Lithium(I), Cadmium(II), and Mercury(II)," *Bull. Chem. Soc. Jpn.* 69:673-677, Nippon Kagakukai (1996).
Tabata, M., et al., "Trace of Analysis of Lithium with a Water-Soluble Porphyrin," *J. Inclusion Phenomena and Mol. Recognit. in Chem.* 32:267-281, Kluwer Academic Publishers (1998).
Tabata, M., et al., "Spectrophotometric determination of lithium ion using a water-soluble octabromoporphyrin in aqueous solution," *Talanta* 46:703-709, Elsevier Science B.V. (1998).

* cited by examiner

*Primary Examiner*—Arlen Soderquist
(74) *Attorney, Agent, or Firm*—Sterne, Kessler, Goldstein & Fox P.L.L.C.

(57) ABSTRACT

A method of detecting soluble lithium in a liquid biological sample comprising combining: (a) an amount of the biological sample; (b) 2,3,7,8,12,13,17,18-octabromo-5,10,15, 20-tetrakis(4-sulphonatophenyl) porphyrin; (c) alkali; (d) detergent; (e) chelating agent; and (f) optionally a suitable solvent; to produce a test sample; detecting absorbance change of the test sample relative to a lithium deficient standard sample at a wavelength of between about 475 nm and about 485 nm, between about 515 nm and about 525 nm or simultaneously between about 475 nm and about 485 nm and between about 515 nm and about 525 nm, wherein absorbance change indicates presence of soluble lithium in the biological sample. Also disclosed is a method of quantitatively measuring soluble lithium ions in a biological sample and a reagent for use in such methods.

39 Claims, 9 Drawing Sheets maximum — 484 nm  A = +0.002 minimum — 5.5 nm  A = -0.008

LITHIUM DETECTION IN LIQUID BIOLOGICAL SAMPLES AND REAGENTS THEREFOR

FIELD OF THE INVENTION

The present invention relates to methods of detecting lithium in liquid biological samples, to methods of quantitatively measuring lithium in liquid biological samples and to the reagents which may be utilised in such methods.

BACKGROUND OF THE INVENTION

Lithium therapy has for many years been adopted for treatment of patients suffering from mania, bipolar disorder and other psychiatric illnesses. Maintenance of lithium ion blood concentration within the therapeutic concentration range of between 0.5 to 1.0 mmol/L within psychiatric patients, generally via administration of lithium ions in the form of lithium carbonate, has been found to be particularly effective in controlling mood in such patients. A difficulty arises however in that the exposure of patients to elevated lithium ion levels (above approximately 1.5 mmol/L) over an extended period contributes to nephrotoxicity and toxicity to the thyroid gland. Acute elevation of physiological lithium levels presents a medical emergency due to nephrotoxicity. It is of course not uncommon for psychiatric patients to either be non-compliant with their lithium medication or to accidentally or intentionally over medicate. For these reasons, and in order to assist medical practitioners in monitoring the effectiveness of lithium therapy in patients, there is a need for simple and cost effective methods by which lithium can be detected and/or for lithium levels to be quantified within biological liquid samples.

Historically lithium levels in serum have been measured by flame emission photometry techniques. In the use of flame emission photometry for sodium and potassium measurement lithium is adopted as the internal standard. Such techniques are modified for lithium measurement with the lithium internal standard being replaced by caesium. Unfortunately, flame emission photometry apparatus using caesium as the internal standard are expensive to acquire and maintain and can be troublesome to operate.

More recently, lithium concentration measurement in biological samples has been conducted by utilising ion selective electrode (ISE) techniques, which involve crown ethers having a core which accommodates the $Li^+$ ion. While early ISE techniques were prone to interferences caused by sodium and other ions present in the test sample, more recent ISE analysers are capable of accurate and precise lithium measurement. Although ISE analysers are less expensive and easier to operate and maintain than flame photometer equipment, other alternative and relatively low cost lithium measurement techniques are desirable.

A number of porphyrin compounds which show high selectivity for metal ions have recently been identified, as for example reported in Richards et al (1) and Tabata et al (2), the disclosures of which are included herein in their entirety by way of reference. Unfortunately, some difficulties have been encountered in utilising the porphyrin compounds identified in the Richards et al and Tabata et al papers in simple and efficient methods for determining the presence of and/or quantifying the levels of lithium in biological liquid samples. In particular, Tabata et al notes that protein reacts with the porphyrin and reduces absorbance, and that as a result serum subjected to the lithium determination method required the removal of protein by use of trichloroacetic acid. The trichloroacetic acid itself then needed to be removed by extraction with diethyl ether. These protein removal steps increase the complexity and cost of the porphyrin based spectrophotometric lithium measurement techniques, effectively precluding the use of the Tabata et al method on automated chemical analysers.

With the above description in mind it is an object of the present invention to provide a method of detecting and/or measuring lithium levels within biological liquid samples which overcome some or all of the above identified problems with prior art techniques. It is also an object of the invention to provide a reagent that can readily be utilised in such techniques. Other objects of the present invention will become apparent from the following detailed description thereof.

SUMMARY OF THE INVENTION

According to one embodiment of the present invention there is provided a method of detecting soluble lithium ions in a liquid biological sample comprising combining:

(a) an amount of the biological sample;
 (b) 2,3,7,8,12,13,17,18-octobromo-5,10,15,20-tetrakis(4-sulphonatophenyl) porphyrin or a non-lithium salt thereof;
 (c) alkali;
 (d) detergent;
 (e) optionally a chelating agent; and
 (f) optionally a suitable solvent;
 to produce a test solution;

detecting absorbance change of the test solution relative to a lithium deficient blank at a wavelength of between about 475 nm and about 495 nm, between about 505 nm and about 525 nm or simultaneously between about 475 nm and about 495 nm and between about 505 nm and about 525 nm, wherein absorbance change indicates presence of soluble lithium ions in the biological sample.

In another embodiment of the present invention there is provided a method of quantitatively measuring soluble lithium ions in a liquid biological sample comprising combining:

(a) a measured volume of the biological sample;
 (b) 2,3,7,8,12,13,17,18-octobromo-5,10,15,20-tetrakis(4-sulphonatophenyl) porphyrin or a non-lithium salt thereof;
 (c) alkali;
 (d) detergent;
 (e) optionally a chelating agent; and
 (f) optionally a suitable solvent;
 to produce a test solution of known volume;
 measuring absorbance change of the test sample relative to a lithium deficient blank at a wavelength of between about 475 nm and about 495 nm, between about 505 nm and about 525 nm or simultaneously between about 475 nm and about 495 nm and between about 505 nm and about 525 nm, and comparing the absorbance change measurement against absorbance change for standard sample having known lithium concentration, to thereby determine soluble lithium ion concentration of the liquid biological sample.

In a further embodiment of the present invention there is provided a reagent for use in a method of detection of soluble lithium ions in a liquid biological sample comprising:

(i) 2,3,7,8,12,13,17,18-octobromo-5,10,15,20-tetrakis(4-sulphonatophenyl) porphyrin or a non-lithium salt thereof;
(ii) alkali;
(iii) detergent;
(iv) optionally a chelating agent; and
(v) optionally a suitable solvent.

Preferably the absorbance change detection or measurement is conducted at a wavelength of about 485 nm, about 515 nm or simultaneously at about 485 nm and about 515 nm.

In a preferred embodiment of the invention the liquid biological sample is plasma, serum, lymph, urine, saliva, tears, milk or is derived from any of these. In particularly preferred embodiments of the invention, the biological sample is plasma or serum.

Preferably the test solution has a pH of at least about 10. Particularly preferably the test solution has a pH of about 13.

In a preferred embodiment of the invention the alkali is aqueous sodium hydroxide which is present in the reagent in a concentration of between about 0.001M to about 0.5M, particularly preferably about 0.10M.

Preferably the 2,3,7,8,12,13,17,18-octobromo-5,10,15, 20-tetrakis(4-sulphonatophenyl) porphyrin is present in the reagent in a concentration of between about 5 mg/L to about 200 mg/L, particularly preferably about 30 mg/L.

In a preferred embodiment of the invention the detergent is a cationic, anionic or non-ionic detergent, preferably an alkylsulphate, a polyoxyethylene ether, an alkanesulphonate or an alkylbenzenesulphonate. In a particularly preferred embodiment of the invention the detergent is BRIJ 35 which may for example be used in the form of a 30% solution within the methods of the invention and may preferably be present within the reagent at a concentration of between about 0.001% to about 4.0% by volume of total reagent volume, preferably about 0.4%.

In preferred embodiments of the invention the chelating agent is ethylenediamine, pyridine, propylenediamine, diethylenetriamine, triethylenetetramine, 2,2'-bipyridine, 1,10-phenanthroline or ethylenediamine tetraacetic acid (EDTA). Preferably the chelating agent is EDTA and particularly preferably it is used in the form of tetrasodium EDTA which may be present in a concentration of between about 1.0 $\mu$M to about 1,000 $\mu$M, preferably about 50 $\mu$M.

Preferably the solvent according to the invention is distilled water, ethanol, methanol, acetone, dimethylformamide or dimethylsulphoxide. Particularly preferably the solvent is dimethylsulphoxide or water.

In a preferred embodiment of the invention the lithium deficient blank includes each of components (b) to (c) and (e) and (f) if present in the test solution, with solvent present in place of component (a).

According to another embodiment of the invention the presence of lithium is indicated by negative absorbance change at about 515 nm and according to a further embodiment of the invention the presence of lithium is indicated by positive absorbance change at about 485 nm.

In another embodiment of the invention the reagent may further comprise a fungicide and/or bactericide. Preferably the fungicide/bactericide is sodium azide which may be present in a concentration of between about 0.1 g/L and about 10 g/L, preferably about 1.0 g/L.

BRIEF DESCRIPTION OF THE FIGURES

The invention is further described by way of example with reference to the figures wherein.

DETAILED DESCRIPTION OF THE INVENTION

Figure 1:
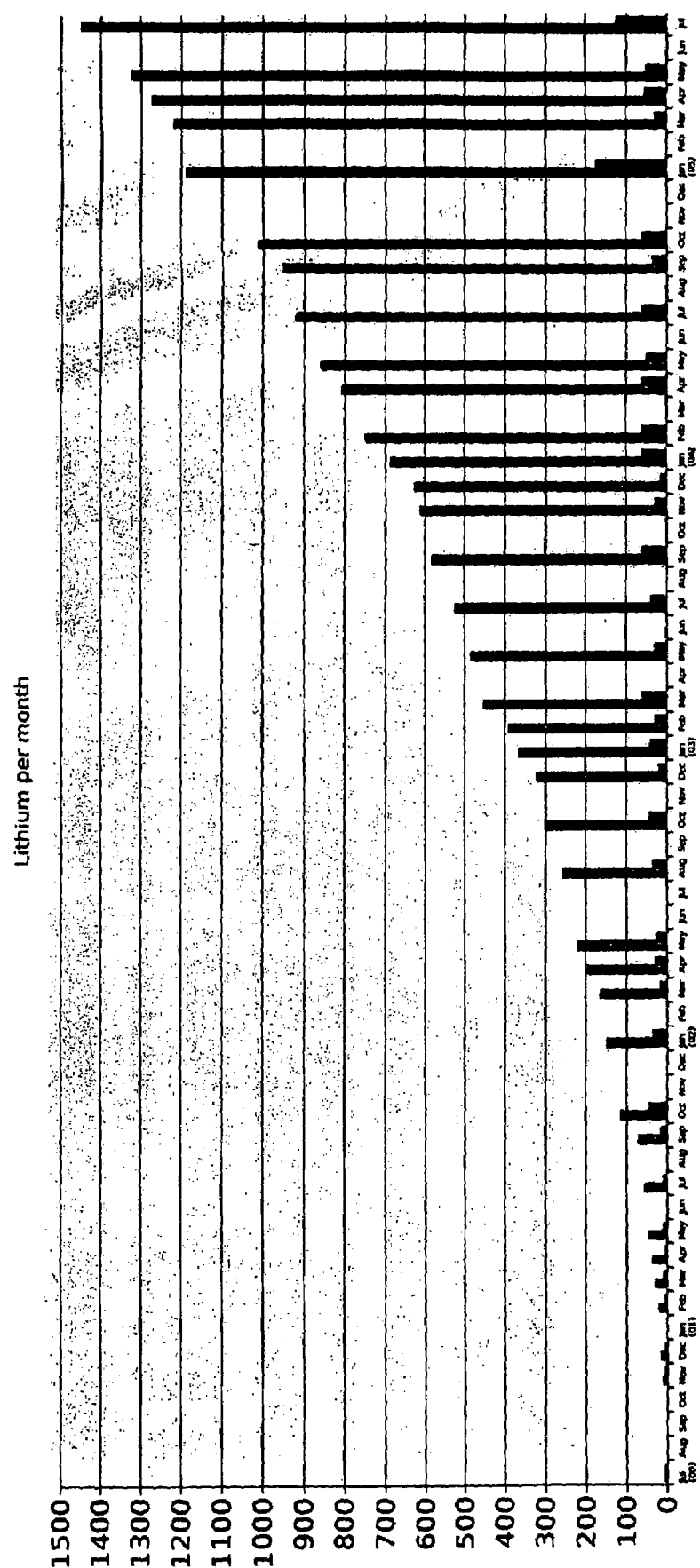
FIG. 1 shows a plot of absorbance change against wavelength for a serum sample (including Li$^+$ at 1 mmol/L) with reagent, compared to a reagent blank (with serum replaced with distilled water).

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The methods according to the present invention can be used either for simply detecting the presence of detectable concentrations of soluble lithium ions in a liquid biological sample, or more particularly to quantify soluble lithium ion concentrations in liquid biological samples. There may be occasions when a simple positive or negative answer regarding the presence of a detectable concentration of lithium in a biological sample is all that is required, such as in the case where it is merely necessary to determine whether a psychiatric patient is complying with a therapeutic lithium prescription. More regularly, however, the methods of the invention will be adopted to accurately monitor physiological levels of lithium to assist a medical practitioner in determining treatment progress of a patient on lithium therapy.

Biological samples which may be utilised according to the methods of the present invention include biological liquids substantially deficient of cells, such as for example blood plasma or serum, lymph (preferably with cells removed), urine, saliva, tears, milk or other samples derived therefrom. For example the methods according to the invention may be conducted on liquid biological samples from the above categories which are fractionated to remove one or other classes of component, such as plasma, serum or lymph fractionated to remove proteinaceous materials.

A key ingredient utilised in the methods and reagents of the present invention is 2,3,7,8,12,13,17,18-octobromo-5,10,15,20-tetrakis(4-sulphonatophenyl)porphyrin (hereinafter referred to as "chromogen"), as depicted in formula I below.

Formula I

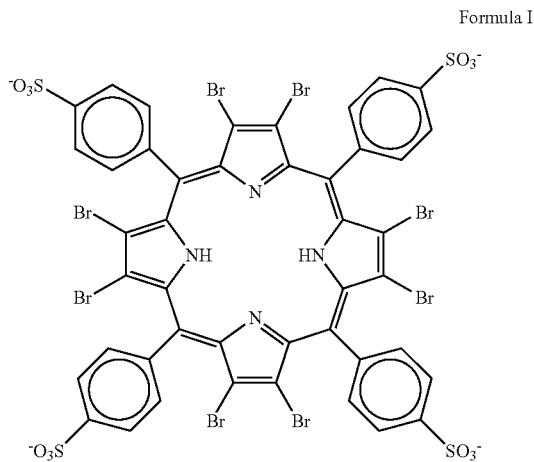

The chromogen can be prepared according to the method of Tabata et al (2). It may be utilised in the form of a salt, but naturally not in the form of a lithium salt. Such salts are also encompassed by the term "chromogen". At alkaline pHs of greater than about 10 the chromogen is deprotonated and is then in a form which allows formation of a $Li^+$/chromogen complex. The formation of a complex between the chromogen and lithium is quite specific due to accommodation of the small ionic radius lithium ion (73 pm) within the chromogen core. Formation of complexes between the chromogen and the larger sodium (113 pm radius) and potassium (151 pm radius) ions have not been observed. As indicated by Tabata et al (2) the chromogen undergoes a spectral change upon formation of a complex with $Li^+$, with an absorbance peak at 490.5 nm. The detection of this spectral change forms the basis of the methods according to the present invention, although as will be further described the present inventors have determined that under the specific conditions outlined herein the wavelength of the absorbance peak is shifted so that the $Li^+$/chromogen complex exhibits an absorbance maximum peak between about 475 nm and about 495 nm and an absorbance minimum peak at between about 505 nm and about 525 nm. Specifically the maximum peak is at about 485 nm (more specifically at about 484.8 nm) and the minimum peak is at about 515 nm (more specifically at about 514.7 nm).

Given that deprotonation of the chromogen is necessary for formation of the lithium/chromogen complex to take place, it is important that the test solution which includes an amount of the biological sample to be tested has a pH of at least about 10. This can of course be achieved by the inclusion of alkali within the test reagent. Examples of particular alkali which may be utilised in this regard include sodium hydroxide, potassium hydroxide, ammonium hydroxide, sodium carbonate and potassium carbonate, although it is to be understood that other alkali may also be utilised. Preferred alkali which may be utilised in this manner are sodium hydroxide and potassium carbonate.

The present inventors have determined that the inclusion of detergent within the reagent of the invention and its utilisation within the inventive methods not only results in increased absorbance intensity measurements of biological samples which include chromogen and lithium, but also results in a shift in the wavelength at which the maximum absorbance is detected. Without wishing to be bound by theory it has been postulated that these characteristics may be explained by the detergent in some way countering the chromogenic effects of protein within the liquid biological sample. Furthermore, and quite surprisingly, following the inclusion of detergent within the reagents of the invention, the present inventors have been able to detect an absorbance minimum peak at between about 505 nm and 525 nm (more specifically at approximately 515 nm) which has not previously been described. This presence of both a minimum and maximum absorbance peak confers upon the present methods both versatility (as wavelength filters of varying descriptions can be utilised) and increased sensitivity relative to prior art methods, as it is possible to take measurements at the wavelengths of both the absorbance maximum and minimum peaks.

A wide variety of detergents may be utilised in accordance with the present invention, including for example cationic, anionic or non-ionic detergents. Examples of classes of detergents that may be utilised include alkylsulphate detergents, polyoxyethylene ethers, alkanesulphonate detergents and alkylbenzenesulphonate detergents. Some specific examples of suitable detergents are Empigen BB AU, Triton X-100, Triton X-405, sodium lauryl sulphate, mixed alkyl trimethyl ammonium bromide and benzethonium chloride. A particularly preferred detergent which may be adopted is BRIJ 35, which constitutes polyoxyethylene 23 laurylether, commercially available from Sigma Chemical Co.

It has also been found effective to include a chelating agent in the reagent according to the invention which, again without wishing to be bound by theory, may assist in eliminating or at least limiting chromogenic interference which may arise due to divalent and trivalent cations. Some examples of chelating agents which may be adopted include ethylenediamine, pyridine, propylenediamine, diethylenetriamine, triethylenetetramine, 2,2'-bipyridine, 1,10-phenanthroline and ethylenediamine tetraacetic acid (EDTA). Preferably the chelating agent adopted is EDTA and in particular, the EDTA utilised may be tetrasodium EDTA.

Depending upon the volumes of components utilised in the detection method or incorporated within the reagents of the invention it may be appropriate to include a suitable solvent. It has surprisingly been found by the present inventors that use of dimethylsulphoxide (DMSO) as a solvent seems to enhance the activity of, and stabilise the porphyrin reagent. Without wishing to be bound by theory it seems that the use of DMSO as solvent may prevent or at least slow degradation of the reagent resulting from exposure to atmospheric carbon dioxide. Another preferred solvent is distilled or otherwise de-ionised water. However, the term "suitable solvent" also includes within its scope water miscible organic solvents. Examples of water miscible organic solvents that may be adopted include methanol, ethanol, acetone, dimethylformamide and dimethylsulphoxide. It is to be stressed, however, that these solvents are referred to by way of example only and that other water miscible organic solvents may equally be utilised. For example it may be necessary to specifically add a suitable solvent to the inventive reagent or when conducting the methods according to the invention if further liquid is required to produce a sample large enough for spectrophotometric analysis. However, as the chromogen and/or alkali and/or detergent and/or chelating agent may often be added in a form already diluted in solvent and indeed because the biological sample itself may also have been diluted with solvent before preparation of the test solution, it may not be necessary to include further solvent either during test solution preparation or in preparation of the reagent.

A reagent which may be used in methods according to the present invention can be prepared in advance of conducting the method and may contain the chromogen, alkali, detergent and optionally a chelating agent and/or a suitable solvent, as outlined above. In one embodiment of the invention the reagent is prepared utilising the chromogen, aqueous sodium hydroxide, an aqueous 30% (v/v) solution of BRIJ 35 and tetrasodium EDTA. The reagent may for example include these components in the following concentrations:

| Component | Concentration |
| --- | --- |
| 2,3,7,8,12,13,17,18-octobromo-5,10,15,20-tetrakis(4-sulphonatophenyl) porphyrin (chromogen) | between about 5 mg/L to about 200 mg/L |
| aqueous sodium hydroxide | between about 0.001 M to about 0.5 M |
| aqueous BRIJ 35 | between about 0.001% to about 4% by volume of total reagent volume |
| tetrasodium EDTA | between about 1.0 µM to about 1,000 µM |

The reagent may additionally include a fungicide and/or bactericide or for that matter other components such as stabilisers, preservatives, anti-oxidants, dyes, pigments or the like. A specific example of a fungicide/bactericide that can conveniently be adopted is sodium azide. In one embodiment of the invention sodium azide is included within the reagent at a concentration of between about 0.1 g/L and about 10 g/L. In one embodiment of the invention the reagent for use in the lithium detection and concentration determination methods according to the present invention will be supplied as a single component, stable liquid. Preferably it will be provided in an opaque container, ready to use.

It is naturally important that the test samples do not include outside sources of lithium that could compromise assay results. For example, lithium heparin plasma must not be utilised as a biological sample within the presently described assay methods.

A preferred reagent according to the present invention includes chromogen at about 30 mg/L, sodium hydroxide at about 0.10M, BRIJ 35 at about 0.4% by volume of total reagent volume, tetrasodium EDTA at about 50 µM, in distilled water. In the case where sodium azide is present it may be included at about 1.0 g/L. In another embodiment water and sodium hydroxide may be replaced with DMSO (for example a solution of 5% to 50%, preferably about 30% by volume) and potassium carbonate (for example about 0.1M).

The detection method according to the invention is conducted by detecting absorbance change of the test sample relative to a lithium deficient blank. The lithium deficient blank may be prepared by following the protocol for preparation of the test solution but replacing the included amount of the biological sample with a suitable solvent. In the case where the method is intended to quantitatively determine lithium concentration it is of course necessary for the volume of the biological sample within the test solution to be accurately measured and to accurately determine the total volume of the test solution. By comparison of absorbance change measured for the test solution against absorbance change for standard samples having known lithium concentration, it is possible to accurately determine the lithium concentration within the test solution and by knowledge of the dilutions from the original biological sample, to make a determination of lithium concentration within the original biological sample. For example, by preparing a plot of absorbance change against lithium concentration for at least two samples having known lithium concentration it is possible to read lithium concentration for test samples from the plot once the absorbance change has been determined. It is also possible to calculate test solution concentration by simply dividing the absorbance change determined for the test solution (containing biological sample) by the absorbance change determined for the standard lithium concentration sample and multiplying the result by the known concentration of the standard lithium sample. Importantly, the absorbance change has been found to be linear for lithium concentrations in the physiological range of up to 3.0 mmol/L of lithium. In the case where it is suspected that the lithium concentration of a biological sample may exceed 3.0 mmol/L then the biological samples should be diluted to bring the test solution concentration to within the analytical range of the assay.

While it is of course possible for the methods according to the present invention to be performed on a manual basis, the present methods may readily be automated by utilising a wide range of clinical chemistry analysers provided that they have a wavelength selection capability of about 485 nm, about 515 nm or the bichromatic pair of wavelengths of about 485 nm and about 515 nm, or at least within the ranges 475-495 nm, 505-525 nm and the corresponding bichromatic pair. Examples of current automated systems which have the appropriate capabilities are the Hitachi models 917, 747, 737, 717, 705, 902 and 912; the Olympus models: Reply, AU5000, AU5200, AU800, AU600 and AU400; the Technicon model: DAX and the Roche models Cobas Bio and Cobas Integra.

In another aspect of the invention the reagent described above may be impregnated into or adsorbed onto a matrix material (for example paper, cardboard, glass or glass fibre, cellulose or any of a range of polymeric materials) to form a test strip. Such a test strip may then be used by medical practitioners or health care workers to instantly test a biological sample of a patient (preferably one obtained in a non-invasive manner, such as urine or saliva), as a means of detecting the presence of lithium ions and determining whether a patient is complying with a lithium prescription. In such cases a visible change of test-strip colour would indicate presence of lithium ions in the tested biological sample. Test strips of this type are disclosed in U.S. Pat. Nos. 3,992,158 and 4,292,272, the disclosures of which are included herein in their entirety by way of reference. A similar analytical tool can be produced in the form of a vial, tube or other preferably disposable device containing liquid reagent of the invention, to which an amount of a biological sample can be added. A colour change of the reagent will again be indicative of the presence of lithium ions in the biological sample.

The present invention will now be described further and by way of example only with reference to the following non-limiting examples:

EXAMPLE 1

Analytical Protocol

1) Dilute one volume of biological liquid sample accurately by addition of 10 volumes of deionised or distilled water.

2) Mix diluted biological sample thoroughly.

3) Take one volume of diluted sample and add 100 volumes of reagent and mix to produce test solution. The reagent comprises chromogen (20 µM) in aqueous sodium hydroxide (pH 13.0), BRIJ 35 detergent (0.4% by volume of total volume of reagent) and tetrasodium EDTA chelating agent (50 µM).

4a) After five minutes at ambient temperature or two minutes at 37° C. read absorbance of test solution at 515 nm against a lithium deficient blank (where the biological liquid is replaced by distilled water) in a spectrophotometer (the inventors used a GBC Cintra 10e spectrophotometer). Record the absorbance change ($\Delta A$) (absorbance of test solution less absorbance of blank), which will be negative.

4b) Alternatively, carry out step 4 with spectrophotometer set at 485 nm. The absorbance change ($\Delta A$) recorded will be positive.

5) The assay can be calibrated by comparison with results obtained by following steps 1 to 4 with a standard of known lithium concentration in place of the biological liquid sample. The solution of known lithium concentration can be either a serum based (matrix matched) material or can be a primary aqueous solution. Ideally the lithium concentration within the standard will approximate 1.00 mM. Calibration accuracy is independent of matrix effects.

6) Concentration calculation can be conducted according to the following formula $$\text{lithium concentration of biological sample} = \frac{\Delta A_w \text{ (test solution)}}{\Delta A_w \text{(known [Li}^+\text{] standard)}} \times conc. \text{ of known lithium standard}$$

where w=wavelength at which absorbance measurements are conducted.

Figure 2:
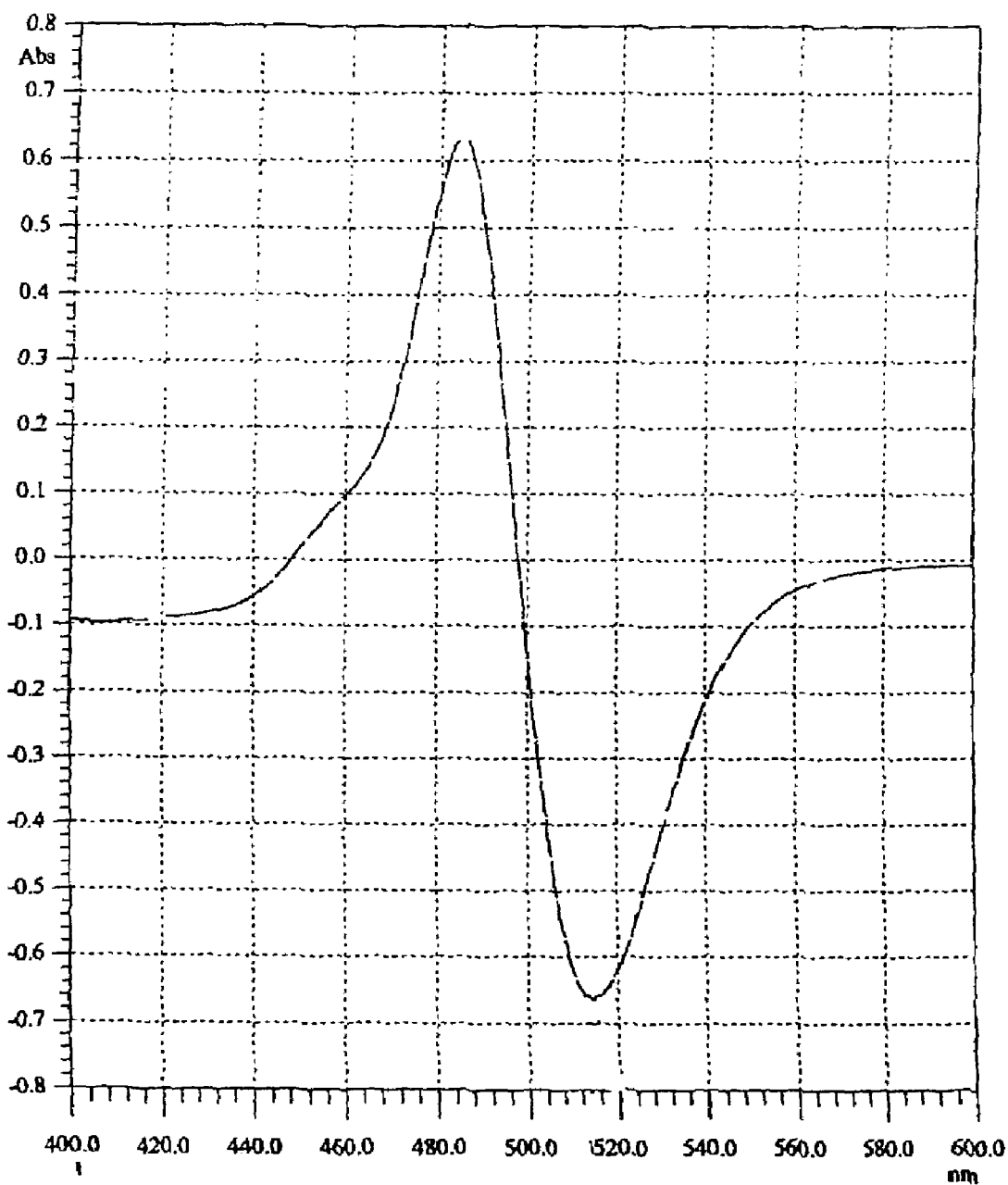
FIG. 2 shows a plot of absorbance change against wavelength for a serum sample (including Li$^+$ at 4 mmol/L) with reagent, compared to a reagent blank (with serum replaced with distilled water).

Plots of absorbance change for serum samples including, and deficient, of lithium are shown in FIGS. 1 to 4. FIGS. 1 and 2 show plots of absorbance change against wavelength for samples prepared according to the protocol outlined above (where the biological sample was serum, with lithium ion concentrations of 1 mmol/L and 4 mmol/L, respectively). In these plots a reagent blank was used which had serum replaced by distilled water.

Figure 3:
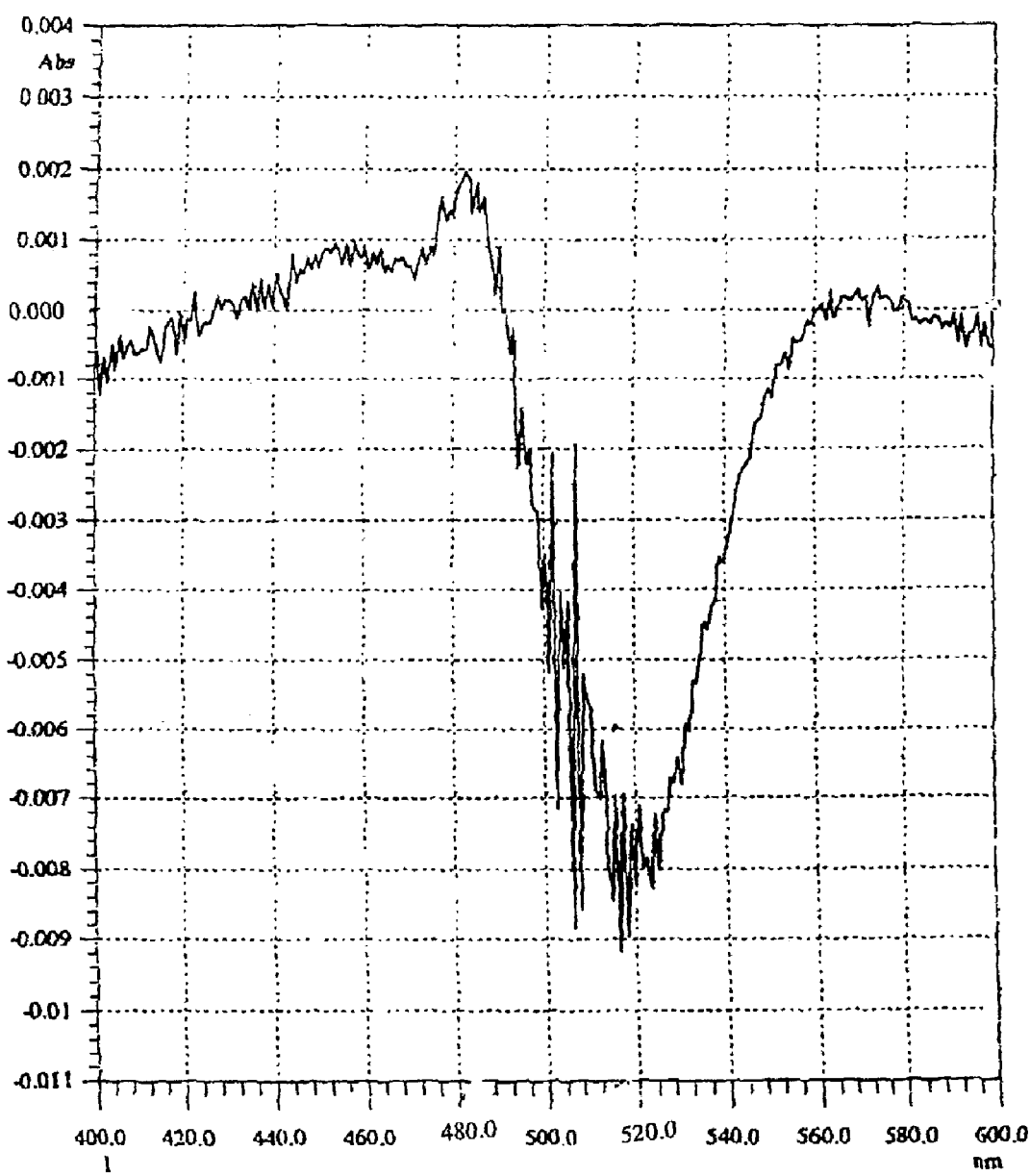
FIG. 3 shows a plot of absorbance change against wavelength for a serum sample (deficient of added Li$^+$) with reagent, compared to a reagent blank (with serum replaced with distilled water).
Figure 4:
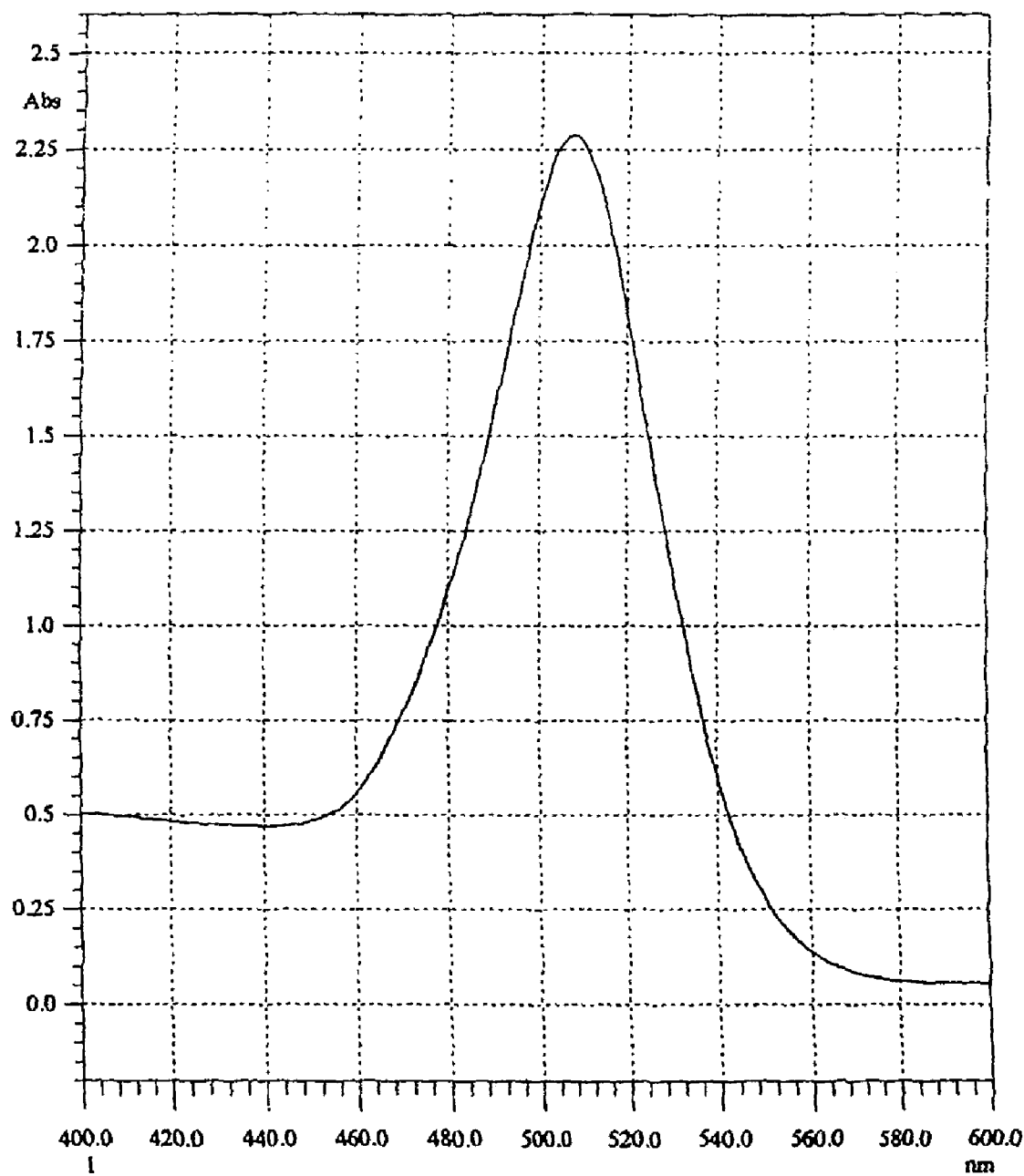
FIG. 4 shows a plot of absorbance change against wavelength for distilled water with reagent, compared to a water blank.

FIGS. 3 and 4 show plots of absorbance change against wavelength for samples prepared according to the protocol outlined above (where the biological sample is serum deficient of added lithium ions) and for distilled water with reagent, respectively. In these plots a reagent blank with serum replaced with distilled water (FIG. 3) and a water blank (FIG. 4) were used. It is noted that in FIG. 3 the maximum and minimum peaks are at much lower absorbance change than for FIGS. 1 and 2. The presence of maximum and minimum peaks within FIG. 3 demonstrates the low concentration of lithium ions (approximately 0.005 mmol/L) naturally present within plasma from a patient who is not on lithium therapy.

EXAMPLE 2

Concentration Determination of Serum Sample Spiked with Known Lithium Chloride Concentrations Lithium chloride at concentrations of 0.50, 1.0, 1.5, 2.0, 2.5, 3.0 and 3.5 mmol/L was spiked into separate samples of human serum. Concentration of $Li^+$ within these serum samples was determined according to the protocol outlined within Example 1. The results are shown in Table 1 below.

TABLE 1

| Theoretical $Li^+$ concentration (mmol/L) | Measured $Li^+$ concentration (mmol/L) | Percentage $Li^+$ detection |
|---|---|---|
| 0.50 | 0.51 | 102% |
| 1.00 | 1.00 | 100% |
| 1.50 | 1.48 | 99% |
| 2.00 | 2.03 | 102% |
| 2.50 | 2.50 | 100% |
| 3.00 | 2.99 | 100% |
| 3.50 | 3.33 | 95% |

The present inventors have determined that the inventive method is extremely sensitive for the measurement of lithium concentrations in serum. The molar absorption coefficient of the lithium/chromogen complex is approximately $9 \times 10^4$. The minimum detection limit for lithium in serum/plasma has been determined to be about 0.04 mmol/L.

The assay has been determined to be linear to approximately 3.0 mmol/L $Li^+$. Samples having concentration greater than this should be further diluted to bring the test solution concentration to within the analytical range of the assay.

The assay has been shown not to be effected by physiological or patho-physiological concentrations of alkali, alkaline earth or transition metals found in human blood. Due to the combination of high sample dilution of the assay and high sensitivity of the chromogen, sample matrix effects such as lipaemia, icterus and haemolysis have negligible effects on assay results at concentrations found in patient specimens.

EXAMPLE 3

Comparison of Assay Results with Flame Emission Spectrophotometry and Ion Selective Electrode Measurements of Lithium Concentration Serum samples 1 to 19 with different $Li^+$ concentrations were measured for lithium concentration utilising flame emission spectrophotometry ("flame") (using an Instrumentation Laboratory Model 943 apparatus), ion selective electrode analysis ("ISE") (using an AVL 9180 Electrolyte Analyser) and by the methods according to the present invention as outlined in Example 1 ("CRLi"). The results are provided in Table 2 below, where all measurements of $Li^+$ are in mmol/L concentration.

TABLE 2

|   | Flame | CRLi | ISE |
|---|---|---|---|
| 1 | 2.23 | 2.33 | 2.31 |
| 2 | 1.93 | 2.04 | 2.03 |
| 3 | 0.86 | 0.84 | 0.89 |
| 4 | 0.44 | 0.49 | 0.49 |

TABLE 2-continued

|    | Flame | CRLi | ISE  |
| -- | ----- | ---- | ---- |
| 5  | 0.80  | 0.79 | 0.84 |
| 6  | 0.28  | 0.32 | 0.27 |
| 7  | 0.68  | 0.63 | 0.72 |
| 8  | 0.50  | 0.60 | 0.49 |
| 9  | 4.73  | 4.67 | 5.17 |
| 10 | 3.65  | 3.54 | 3.80 |
| 11 | 1.61  | 1.66 | 1.67 |
| 12 | 0.73  | 0.83 | 0.81 |
| 13 | 1.28  | 1.28 | 1.29 |
| 14 | 0.09  | 0.13 | 0.13 |
| 15 | 0.78  | 0.85 | 0.82 |
| 16 | 0.20  | 0.25 | 0.24 |
| 17 | 0.38  | 0.41 | 0.41 |
| 18 | 0.54  | 0.55 | 0.55 |
| 19 | 2.00  | 2.03 | 2.08 |

Figure 5:
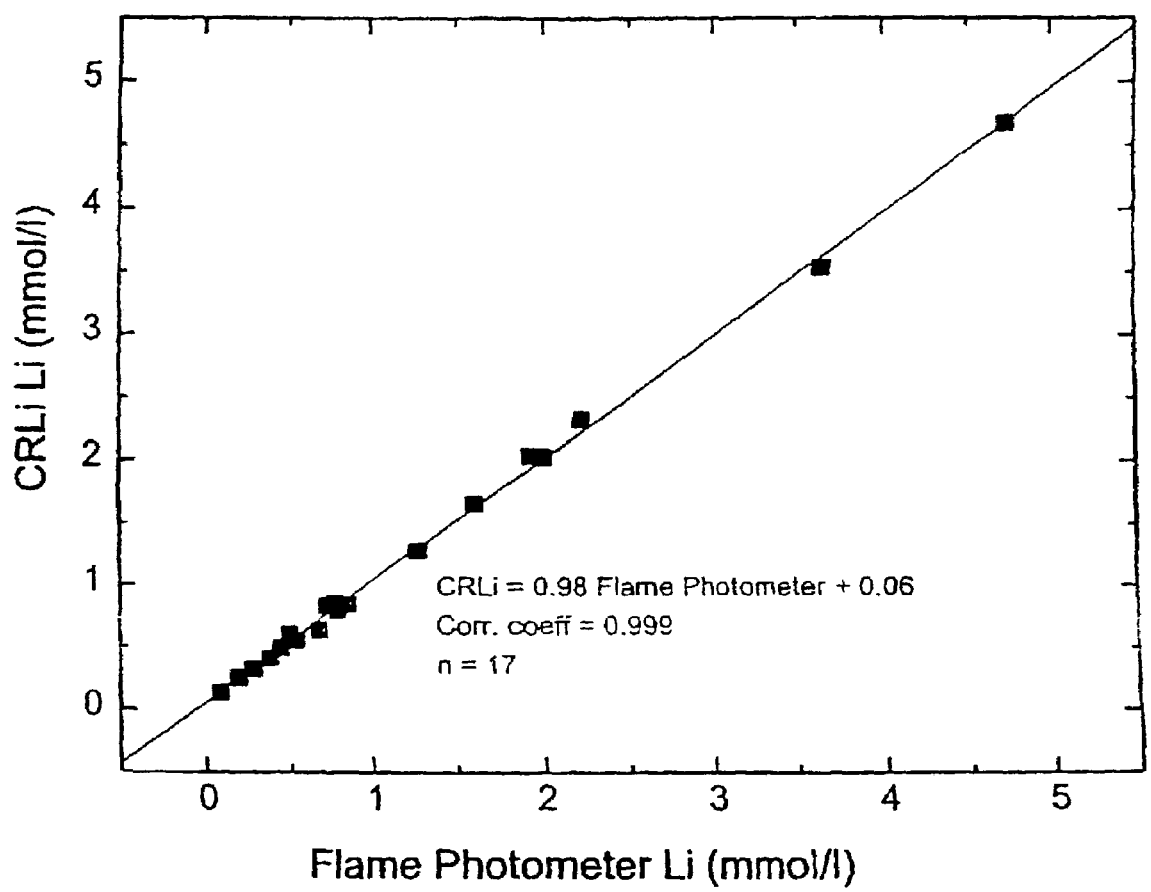
FIG. 5 shows a plot of lithium concentration determined by methods of example 1 (CRLi) (mmol/L) against lithium concentration determined by Flame photometry (mmol/L).
Figure 6:
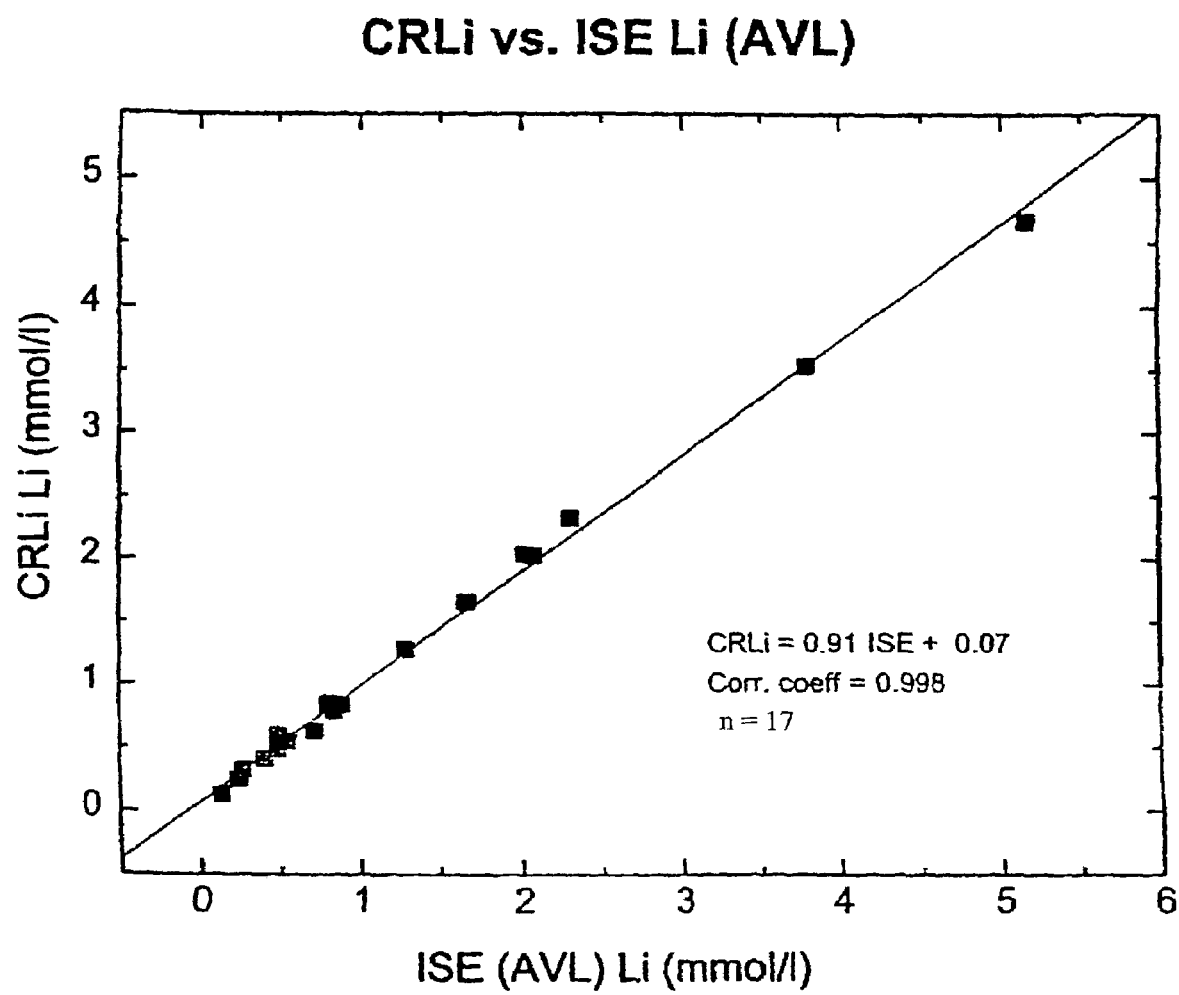
FIG. 6 shows a plot of lithium concentration determined by methods of example 1 (CRLi) (mmol/L) against lithium concentration determined by Ion Selective Electrode analysis (ISE) (mmol/L).

Plots of CRLi lithium measurement against flame photometer lithium measurement and CRLi lithium measurement against ion selective electrode lithium measurement are shown in FIGS. 5 and 6, respectively. The correlations are as follows:

Correlation:

CRLi=0.98 Li (Flame phot.)+0.06 r=0.999 n=17

CRLi=0.91 (ISE)+0.07 r=0.998 n=17

EXAMPLE 4

Automated Analysis

Samples of Biorad Liquicheck Quality Control Serum 1 and 2 were diluted using hand-held automatic pipettes (Finnpipettes); 1 part Q C serum to 10 parts deionized water.

The diluted sample was then aliquoted into 10× Cobas sample cups of Biorad QC 1 and 10× cups of Biorad QC 2.

These were then analysed in two "runs", giving 20 assay results for each material.

Calibrators were 1/11 dilutions of Lithium Standard, 0.50, 1.00 and 3.00 mmol/L concentration.

Using a Cobas Bio Centrifugal Analyser (Roche) the following within run imprecision was obtained:

|      | Low control  | High control |
| ---- | ------------ | ------------ |
| Mean | 0.53 mmol/l  | 1.92 mmol/l  |
| S.D. | 0.016 mmol/l | 0.02 mmol/l  |
| C.V. | 3.0%         | 1.0%         |
| n    | 20           | 20           |

It can be seen on this basis that the assay method of the present invention is well suited to automation.

It is to be understood that the present invention has been described by way of example only and that modifications and/or alterations thereto, which would be apparent to a person skilled in the art based upon the disclosure herein, are also considered to fall within the scope and spirit of the invention.

EXAMPLE 5

Comparison of Solvent Effects on Reagent Stability

It was intended to determine whether the use of a combination of a carbon dioxide resistant alkali (such as potassium carbonate) and the solvent DMSO could improve and stabilise the reagent formulation.

Experimental protocol as follows:

1) Reagents were made with normal formulation (water/NaOH (0.1M)) and 40 mg/l porphyrin and trial formulation (30% DMSO/potassium carbonate (0.1M)) and 34 mg/l porphyrin. (note: as a result of enhanced absorbance in the presence of DMSO, only 34 mg/l of porphyrin required to give equivalent absorbance of 40 mg/l porphyrin in water/NaOH version). Both solutions had a peak absorbance of 2.5 A +/−0.05.

Figure 7:
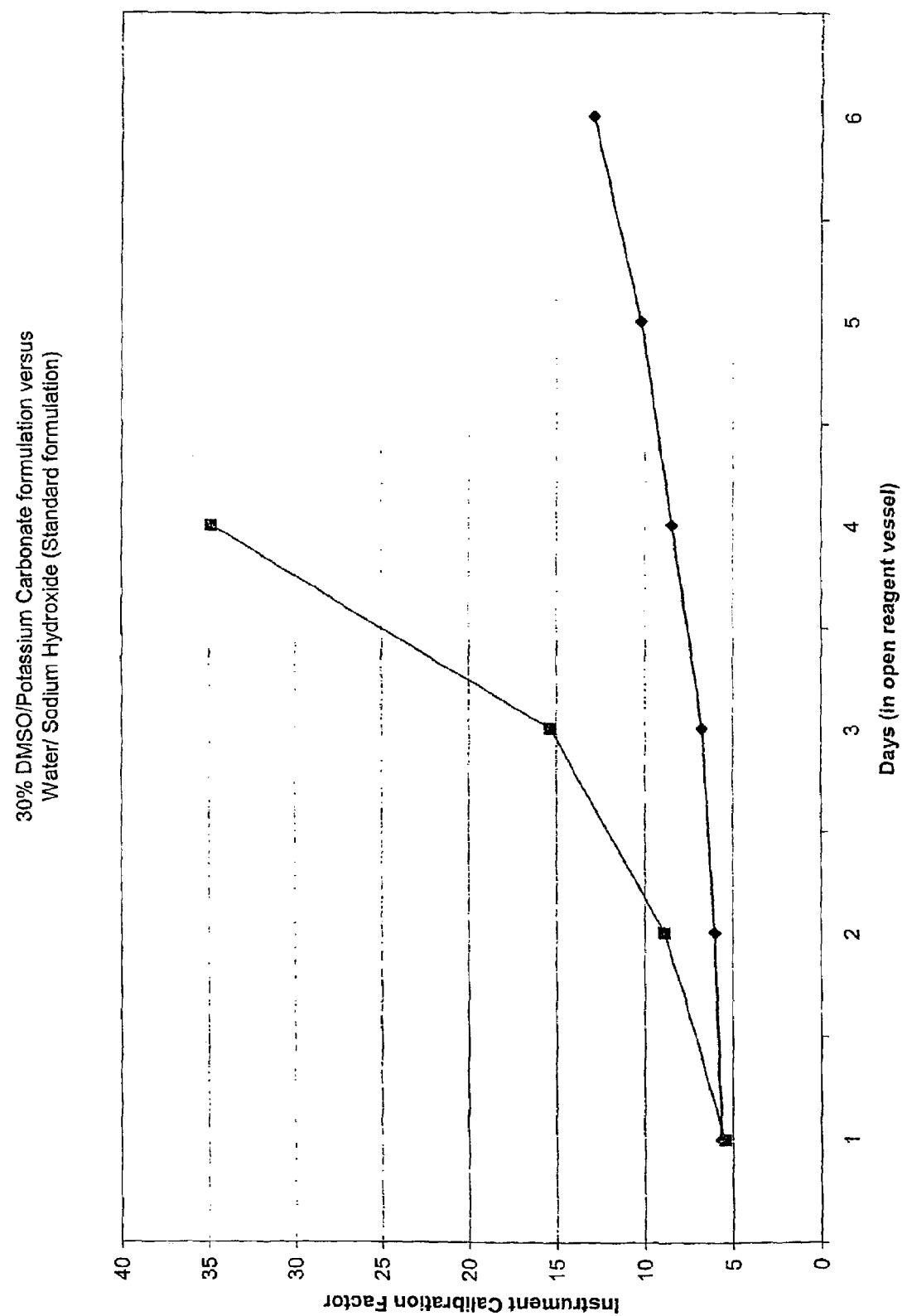
FIG. 7 shows a plot of instrument calibration factor against time of exposure to the atmosphere in an open reagent vessel (days) for a porphyrin/water/sodium hydroxide formulation (standard formulation) in comparison to a porphyrin/DMSO/potassium carbonate formulation.

2) The two reagent solutions were kept in the dark at room temperature in open reagent containers and thus exposed to atmospheric carbon dioxide. Previous experience has shown that strongly alkaline solutions rapidly absorb carbon dioxide from the atmosphere thus resulting in a fall in the solution's pH. As the reagent pH falls the calibration factor increases (calibration factor is the inverse of the absorbance change per mmol of lithium. It gives a measure of sensitivity of the reagent, such that increasing calibration factor reflects decreasing reagent sensitivity.). Eventually, below a certain pH the reagent no longer accurately recovers lithium results from the samples. The results are shown in FIG. 7 where the diamond shaped points are for the DMSO formulation and the square points are for the normal formulation 3) Both solutions were used to analyse a series of aqueous lithium solutions and human serum samples containing lithium.

4) The samples were analysed by both reagents on days one through to six (note: after day 4 the water/NaOH formulation returned erroneous results on the aqueous solutions and patient samples)

5) Results: At day six the DMSO/potassium carbonate formulation still returned satisfactory analytical results. The water/NaOH version was unsuitable for use beyond day 4

EXAMPLE 6

Improved Chromogenicity with DMSO Solvent

Figure 8:
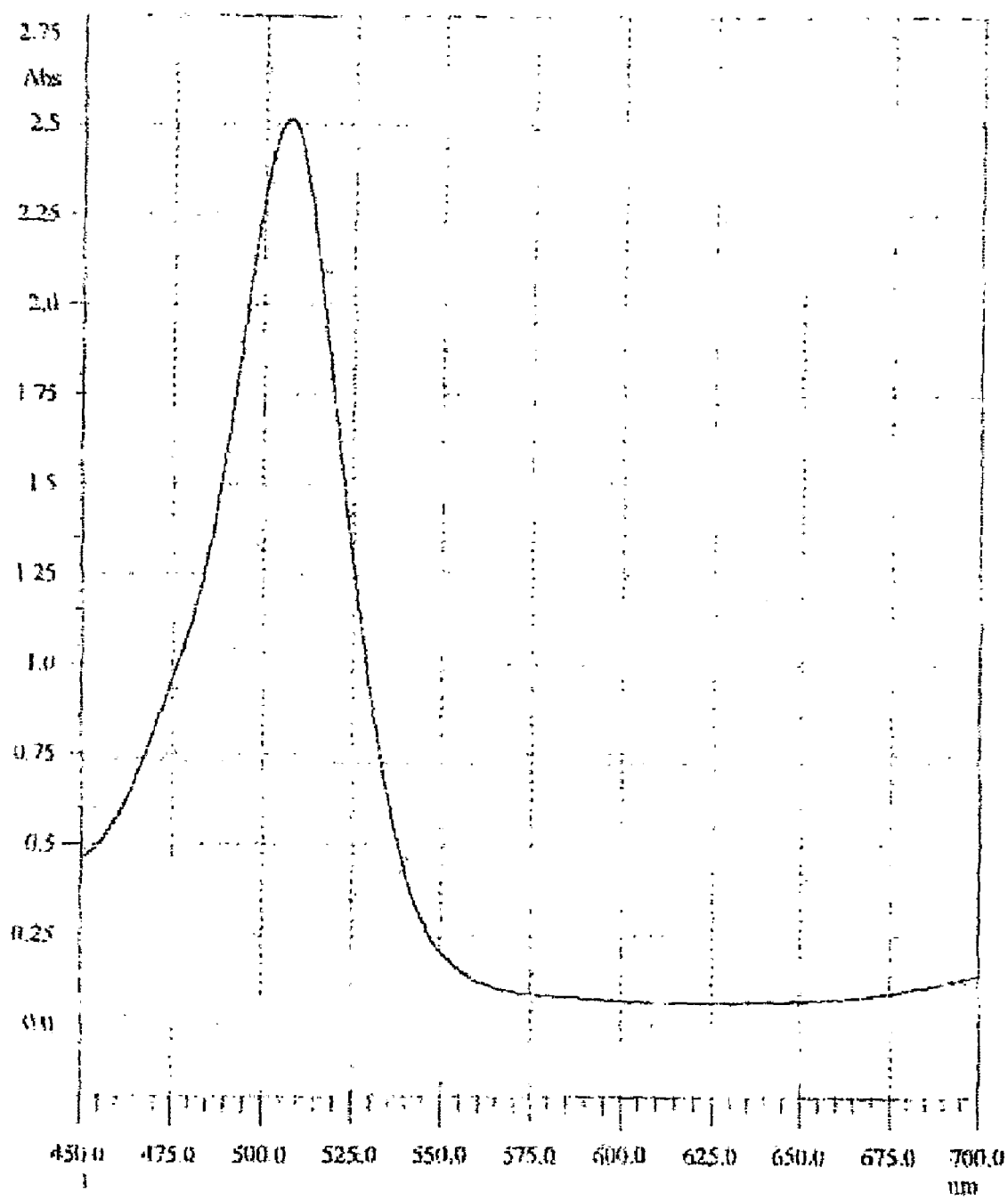
FIG. 8 shows a plot of absorbance against wavelength for a porphyrin/water/sodium hydroxide formulation.
Figure 9:
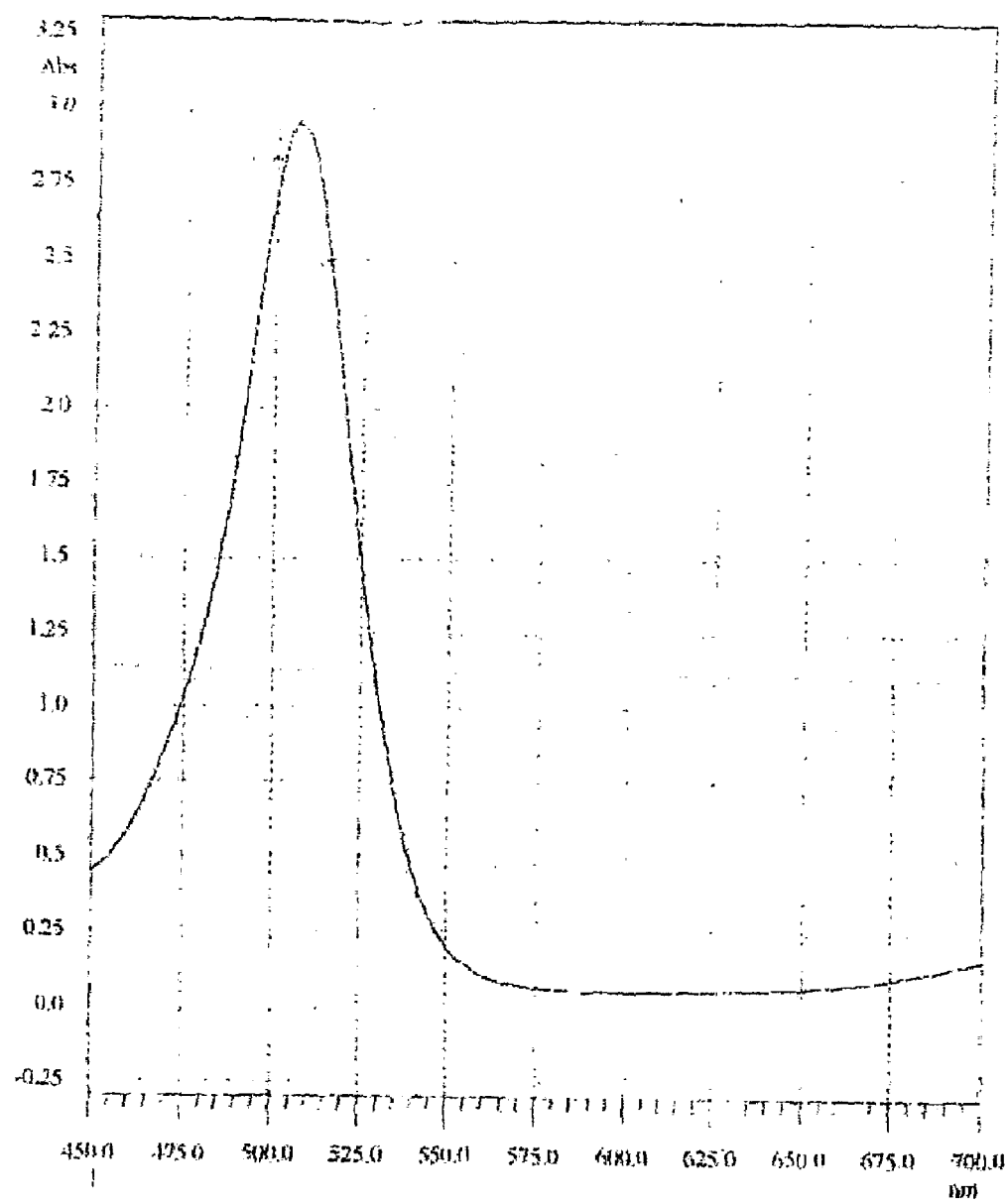
FIG. 9 shows a plot of absorbance against wavelength for a porphyrin/DMSO/potassium carbonate formulation.

FIGS. 8 and 9 show absorbance readings against wavelength for a normal formulation (FIG. 8) and a DMSO formulation (FIG. 9). The normal formulation included water as solvent and 0.1M sodium hydroxide, while the DMSO formulation included 30% DMSO with 0.1M potassium carbonate. Both formulations included 40 mg/L of porphyrin. As can be seen from a comparison of the absorbance maxima from FIGS. 8 and 9, the absorance at 508 nm is approximately 2.95 for the DMSO formulation compared to approximately 2.5 for the normal formulation. This clearly demonstrates enhanced chromogenicity of the DMSO formulation, which is believed by the present inventors to be a separate effect to the improved stability shown in example 5 above.

The invention claimed is:

1. A method of detecting soluble lithium in a liquid biological sample comprising combining:
   (a) an amount of the biological sample;
   (b) 2,3,7,8,12,13,17,18-octobromo-5,10,15,20-tetrakis(4-sulphonatophenyl) porphyrin;
   (c) alkali;

(d) detergent;
(e) chelating agent; and
(f) optionally a suitable solvent;
to produce a test sample having a pH of at least about 10;
detecting absorbance change of the test sample relative to a lithium deficient standard sample at a wavelength of between about 475 nm and about 485 nm, between about 515 nm and about 525 nm or simultaneously between about 475 nm and about 485 nm and between about 515 nm and about 525 nm, wherein absorbance change indicates presence of soluble lithium in the biological sample; with the proviso that the method does not include removal of protein.

2. The method according to claim 1 wherein absorbance change is detected at about 480 nm, at about 520 nm or simultaneously at about 480 nm and about 520 nm.

3. The method according to claim 1 wherein the liquid biological sample is plasma, serum, lymph, urine, saliva tears or milk or wherein the liquid biological sample is derived therefrom.

4. The method according to claim 1 wherein the test sample pH is about 13.

5. The method according to claim 1 wherein the alkali is sodium hydroxide or potassium carbonate.

6. The method according to claim 1 wherein the detergent is a cationic, anionic or non-ionic detergent.

7. The method according to claim 1 wherein the detergent is an alkylsulphate, a polyoxyethylene ether, an alkanesulphonate or an alkylbenzenesulphonate.

8. The method according to claim 1 wherein the detergent is polyoxyethylene 23 laurylether.

9. The method according to claim 1 wherein the chelating agent is ethylenediamine, pyridine, propylenediamine, diethylenetriamine, triethylenetetramine, 2,2'-bipyridine, 1,10-phenanthroline, ethylenediamine tetraacetic acid (EDTA), dimethylglyoximato, glycinato or acetylacetonato.

10. The method according to claim 1 wherein the chelating agent is EDTA.

11. The method according to claim 1 wherein the solvent is distilled water, ethanol, methanol, acetone, dimethylformamide or dimethylsulphoxide.

12. The method according to claim 1 wherein the lithium deficient standard includes each of components (b) to (e) and (f) if present in the test sample, with a suitable solvent present in place of component (a).

13. The method according to claim 1 wherein lithium is indicated by negative absorbance change at about 520 nm.

14. The method according to claim 1 wherein lithium is indicated by positive absorbance change at about 480 nm.

15. A reagent for use in a method of detection of lithium in a liquid biological sample comprising:
(i) 2,3,7,8,12,13,17,18-octobromo-5,10,15,20-tetrakis(4-sulphonatophenyl) porphyrin;
(ii) alkali;
(iii) detergent;
(iv) chelating agent; and
(v) optionally a suitable solvent;
wherein the reagent has a pH of at least about 10.

16. The reagent according to claim 15 wherein component (i) is present in a concentration of between about 5 mg/L to about 200 mg/L.

17. The reagent according to claim 15 wherein the alkali is aqueous sodium hydroxide or potassium carbonate.

18. The reagent according to claim 17 wherein the alkali is present in a concentration of between about 0.001M to about 0.5M.

19. The reagent according to claim 15 wherein the detergent is polyoxyethylene 23 laurylether (about 30% solution (v/v)).

20. The reagent according to claim 19 wherein the polyoxyethylene 23 laurylether is present in a concentration of between about 0.001% to about 4.0% by volume of total reagent volume.

21. The reagent according to claim 15 wherein the chelating agent is ethylenediamine tetraacetic acid (EDTA).

22. The reagent according to claim 21 wherein the EDTA is tetrasodium EDTA present in a concentration of between about 1.0 μM to about 1.000 μM.

23. The reagent according to claim 15 further comprising a fungicide and/or bactericide.

24. The reagent according to claim 23 wherein the fungicide/bactericide is sodium azide.

25. The reagent according to claim 24 wherein the sodium azide is present in a concentration of between about 0.1 g/L and about 10 g/L.

26. The reagent according to claim 25 further comprising about 1.0 g/L of sodium azide.

27. The reagent according to claim 15 comprising:
(i) about 31 mg/L of 2,3,7,8,12,13,17,18-octobromo-5,10,15,20-tetrakis(4-sulphonatophenyl) porphyrin;
(ii) about 0.10M of sodium hydroxide;
(iii) about 0.4% by volume of total reagent volume of polyoxyethylene 23 laurylether;
(iv) about 50 μM of tetrasodium EDTA.

28. A method of quantitatively measuring soluble lithium in a liquid biological sample comprising combining:
(a) a measured volume of the biological sample;
(b) 2,3,7,8,12,13,17,18-octobromo-5,10,15,20-tetrakis(4-sulphonatophenyl) porphyrin;
(c) alkali;
(d) detergent;
(e) chelating agent; and
(f) optionally a suitable solvent;
to produce a test sample of known volume having a pH of at least about 10;
measuring absorbance change of the test sample relative to a lithium deficient standard sample at a wavelength of between about 475 nm and about 485 nm, between about 515 nm and about 525 nm or simultaneously between about 475 nm and about 485 nm and between about 515 nm and about 525 nm, and comparing the absorbance change measurement against plot of absorbance change for samples having known lithium concentration, to thereby determine soluble lithium concentration of the liquid biological sample; with the proviso that the method does not include removal of protein.

29. The method according to claim 28 wherein absorbance change is detected at about 480 nm, at about 520 nm or simultaneously at about 480 nm and about 520 nm.

30. The method according to claim 28 wherein the liquid biological sample is plasma, serum, lymph, protein, urine, saliva, tears, milk or is derived from one of the above.

31. The method according to claim 28 wherein the test sample pH is about 13.

32. The method according to claim 28 wherein the alkali is aqueous sodium hydroxide or potassium carbonate.

33. The method according to claim 28 wherein the detergent is a cationic, anionic or non-ionic detergent.

34. The method according to claim 28 wherein the detergent is an alkylsulphate, a polyoxyethylene ether, an alkanesulphonate or an alkylbenzenesulphonate.

35. The method according to claim 28 wherein the detergent is polyoxyethylene 23 laurylether.

36. The method according to claim 28 wherein the chelating agent is ethylenediamine, pyridine, propylenediamine, diethylenetriamine, triethylenetetramine, 2,2'-bipyridine, 1,10-phenanthroline, ethylenediamine tetraacetic acid (EDTA), dimethylglyoximato, glycinato or acetylacetonato.

37. The method according to claim 28 wherein the chelating agent is EDTA.

38. The method according to claim 28 wherein the solvent is distilled water, ethanol, methanol, acetone, dimethylformamide or dimethylsulfoxide.

39. The method according to claim 28 wherein the lithium deficient standard includes each of components (b) to (e) and (f) if present in the test sample, with a suitable solvent present in place of component (a).

* * * * *